United States Patent [19]

Inoue et al.

[11] Patent Number: 4,824,998

[45] Date of Patent: Apr. 25, 1989

[54] PROCESS FOR PRODUCING TAU-BUTYL METHACRYLATE

[75] Inventors: Kazutaka Inoue; Toshihiro Sato; Masao Kobayashi, all of Otake, Japan

[73] Assignee: Mitsubishi Rayon Co., Ltd., Tokyo, Japan

[21] Appl. No.: 122,453

[22] Filed: Nov. 19, 1987

[30] Foreign Application Priority Data

Nov. 27, 1986 [JP] Japan ................................ 61-282990

[51] Int. Cl.$^4$ ............................................ C07C 69/52
[52] U.S. Cl. ................................................ 560/205
[58] Field of Search ......................................... 560/205

[56] References Cited

U.S. PATENT DOCUMENTS 2,636,049  4/1953  Crawford ............................. 560/205
3,262,993  7/1966  Hagemeyer et al. ................. 560/205
3,875,212  4/1975  Ohsui et al. ......................... 560/205

FOREIGN PATENT DOCUMENTS 2411901  10/1975  Fed. Rep. of Germany .
45-28969  9/1970  Japan .
46-16725  5/1971  Japan .
49-46601  12/1974  Japan .
1108796   4/1968  United Kingdom .

OTHER PUBLICATIONS

Oda, Y et al., Hydrocarbon Process 54(10) 115–17, 1975.

Primary Examiner—Paul J. Killos
Attorney, Agent, or Firm—Oblon, Fisher, Spivak, McClelland & Maier

[57] ABSTRACT

A process for producing methacrylic acid which comprises reacting methacrylic acid and isobutylene in the presence of a sulfonic acid group-containing ion exchange resin by a continuous process while controlling the reaction at a reaction temperature of $-20°$ C. to $+20°$ C. so as to fulfil the following relation:

$$y < 100 - 50x$$

wherein x is the ratio of the total molar number of isobutylene and its reaction products to the total molar number of methacrylic acid and its reaction products and y is conversion (%) of isobutylene, followed by degassing the unreacted isobutylene, distilling off the low boiling substances by distillation under reduced pressure, and then sending the remainder to a t-butyl methacrylate purifying tower where a product of high purity is obtained from the distillate side and unreacted methacrylic acid is withdrawn from the tower bottom side and circulated into the reaction step.

5 Claims, 1 Drawing Sheet

PROCESS FOR PRODUCING TAU-BUTYL METHACRYLATE

FIELD OF THE INVENTION

The present invention relates to a process for producing t-butyl methacrylate by the reaction of methacrylic acid and isobutylene. t-Butyl methacrylate is an ester compound which is industrially manufactured today. Having a polymerizability similar to that of other methacrylic esters and acrylic esters, it is widely used practically as a constitutent of various acrylic coating materials. Particularly because of the excellent miscibility with other substances and low moisture absorption of monomer and the high heat resistance of its polymer, its use is expected to expand more and more.

DESCRIPTION OF RELATED ART

As is well known, t-butyl methacrylate is difficult to be produced according to the conventional synthetic methods of ester compounds such as the esterification using an acid and an alcohol or the transesterification process. From many years ago, it has been synthesized by the addition reaction of isobutylene to methacrylic acid in the presence of a strongly acidic catalyst.

Today, the process using a homogeneous acid catalyst such as sulfuric acid disclosed in British Pat. No. 814,360 is employed industrially. Though yield of this reaction reaches about 80%, this process naturally requires a step for removing the catalyst by neutralization after the reaction, which causes a hydrolysis and a thereby caused decrease in product yield. Further, the separation of by-product is accompanied by a marked decrease in yield. As the result, the product yield is low and the cost is high. Further, this process requires to use an expensive corrosion resistant reactor and the reaction forms a large amount of waste water, so that this process is disadvantageous industrially.

On the other hand, U.S. Pat. No. 3,037,052 discloses a process using a sulfonic acid group-containing ion exchange resin as catalyst. Actually, however, this process yields a large amount of by-product called isobutylene oligomer or oligomers formed by the oligomerization of isobutylene. When these oligomers are formed in a large amount, it incurs a problem regarding the step of purification. That is, it has been found that separation of triisobutylene which is one of the oligomers by distillation is accompanied by a great loss in the useful t-butyl methacrylate and methacrylic acid and therefore the yield of main product is unsatisfactory, so that this process has not yet been established as an effective industrial process. Thus, as a synthesis of t-butyl esters from general carboxylic acids and isobutylene, the process disclosed in the above-mentioned U.S. Patent can be effective only when the isobutylene oligomer formed as a by-product can easily be separated from the carboxylic acid and the t-butyl carboxylate. In the production of t-butyl methacrylate which is the objective compound of the invention, the separation is difficult to practise, so that this process is not yet established as an industrially utilizable process.

As above, in the synthesis of t-butyl methacrylate by the reaction of methacrylic acid and isobutylene, oligomerization of isobutylene takes place as a side reaction to lower the product yield.

Among the oligomers of isobutylene, triisobutylene has a boiling point higher than that of the objective t-butyl methacrylate and lower than that of starting methacrylic acid, and the differences between these boiling points are small. Thus, separation of triisobutylene by distillation requires a high technique. In the process of this distillation, the objective t-butyl methacrylate and methacrylic acid which are useful components are lost to result in an elevation of the cost of t-butyl methacrylate.

Oligomerization of isobutylene takes place easily particularly in the heterogeneous catalytic reaction using sulfonic acid group-containing ion exchange resin rather than in the homogeneous catalytic reaction using sulfuric acid and the like. Among the many possible reasons for this fact, one reason is probably that the heat of reaction generated in the catalyst particles cannot be removed effectively.

Thus, in the production of t-butyl methacrylate from methacrylic acid and isobutylene using sulfonic acid group-containing ion exchange resin as a catalyst, the most important problem is to find out the optimum reaction conditions capable of suppressing the formation of triisobutylene by-product to such small an extent as to make the separation by distillation substantially unnecessary, and to develop a general production process of t-butyl methacrylate on its basis.

SUMMARY OF THE INVENTION

The present inventors conducted many studies on the production of t-butyl methacrylate by the reaction of methacrylic acid and isobutylene using sulfonic acid group-containing ion exchange resin as a catalyst to research into reaction conditions and method of reaction capable of suppressing the formation of by-products, particularly triisobutylene, to a small amount. Further, the inventors studied on the method for taking out the objective t-butyl methacrylate from the resulting reaction product with a high efficiency. As the result, it was found that, if the reaction is carried out according to a continuous process and molar ratio of isobutylene to methacrylic acid, reaction temperature and conversion of reaction in the process of reaction are kept in specified ranges, each of the unreacted starting compounds, by-products and t-butyl methacrylate can be separated with high efficiency, and the t-butyl methacrylate can be obtained in a high purity and high yield, and the process is highly economical. Based on this finding, the present invention was accomplished.

BRIEF DESCRIPTION OF THE DRAWINGS

Next, the drawings attached will be briefly explained below.

Figure 1:
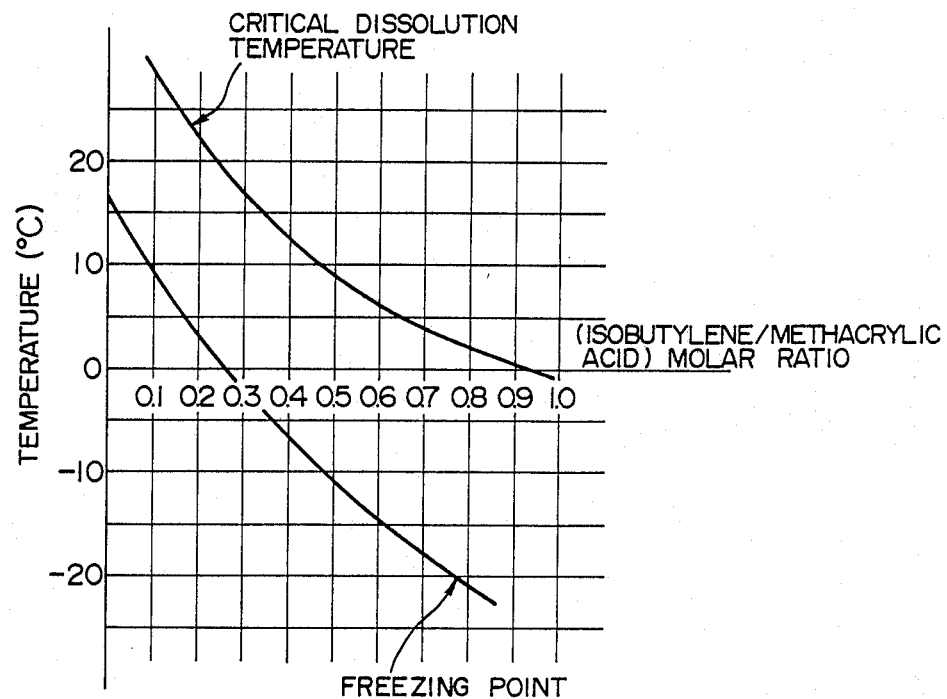
FIG. 1 is a graph illustrating the relations between molar ratio, critical dissolution temperature and freezing point in isobutylene/methacrylic acid system.

1 --- Line
2 --- Line
3 --- Absorbing tower
4 --- Line
5 --- Reactor
6 --- Line
7 --- Degassing plant
8 --- Line
9 --- Line
10 --- Degassing plant 11 --- Line
12 --- Low boiling fraction stripping tower
13 --- Line
14 --- Line
15 --- Line
16 --- t-Butyl methacrylate purifying tower
17 --- Line
18 --- Line
19 --- Line
20 --- Line

DESCRIPTION OF THE PREFERRED EMBODIMENT

Thus, the present invention relates to a process for producing t-butyl methacrylate which comprises reacting methacrylic acid and isobutylene by a continuous process in the presence of a sulfonic acid group-containing ion exchange resin while controlling the reaction at a reaction temperature of $-20°$ C. to $+20°$ C. so as to satisfy the following condition:

$$y < 100 - 50x$$

wherein x is the ratio of total molar number of isobutylene and reaction products of isobutylene to the total molar number of methacrylic acid and reaction products of methacrylic acid and y is conversion (%) of isobutylene, followed by degassing the unreacted isobutylene, subsequently stripping off the low boiling substances by distillation under a reduced pressure, then taking out the objective product having a high purity from the distillate side of a t-butyl methacrylate purifying tower, and withdrawing the unreacted methacrylic acid from the tower bottom side and circulating it into the reaction zone.

One of the characteristic features of the present invention consists in that the reaction is carried out by a continuous process. A batch-wise practice of the reaction is disadvantageous in the following respects. Thus, after completion of the reaction, the sulfonic acid group-containing ion exchange resin catalyst from which the reaction product has been separated still contains a quantity of reaction mixture, and in this remaining reaction mixture oligomers of isobutylene are additionally formed. This results in a decrease in the yield of objective t-butyl methacrylate after repeated use of the catalyst. Further, in the step for separating the by-products such as triisobutylene and the like by distillation, the increased amount of by-product causes an increased loss in the useful components.

Next, the reaction of the invention carried out as a continuous process will be detailed below. In the process of the invention, a solvent may be added to the reaction system. As the solvent used for this purpose, those which are miscible with methacrylic acid, isobutylene and their reaction products and inert with them and exercise no adverse influence on the step for purifying t-butyl methacrylate by distillation are preferable. The reaction product itself may also be selected as the solvent. Concretely saying, low boiling solvents such as n-hexane, benzene, chloroform, methylene chloride and the like and high boiling solvents such as isopropylbenzene, diethylbenzene, amylbenzene and the like are usable for this purpose. The solvent is not limited to the above-mentioned ones, so far as it has the properties mentioned above. As above, if a solvent is added to the reaction system, a uniform reaction product can easily be obtained under the desired conditions. Further, the freezing point of reaction mixture becomes lower and freezing of reaction mixture can easily be avoided even if the reaction is carried out at a low temperature. Further, the removal of heat of reaction becomes easier to practise, so that an improvement in the selectivity of reaction can be expected.

On the other hand, the use of solvent makes the process more complicated, because the solvent must be recovered. Therefore, whether solvent is used or not used should be selected with consideration of the balance of overall process. The process of the invention can also be practised in the absence of solvent. When isobutylene is dissolved into methacrylic acid having a freezing point of 16° C., the relations of the molar ratio [isobutylene/methacrylic acid] in the solution to the critical dissolution temperature and the freezing point of solution are as shown in FIG. 1, according to the results of the experiments of the present inventors.

FIG. 1 demonstrates that a uniform solution can be prepared without using any solvent if procedure of dissolution is carried out at a temperature not higher than the critical dissolution temperature and not lower than the freezing point at the molar ratio adopted. If this dissolution is carried out by contacting isobutylene with a part or the whole of the process fluid, solubility of isobutylene becomes higher so that the critical dissolution temperature becomes higher than in FIG. 1 and the freezing point descends owing to freezing point depression. That is, by such a procedure, the allowable range of dissolution procedure can be broadened.

Needless to say, the procedure of dissolution is easier in a reaction at elevated pressure than in a reaction at ordinary pressure.

When the dissolution is carried out at temperature and pressure at which isobutylene can be fed in liquid state, the dissolution can be realized by merely mixing together isobutylene and methacrylic acid or process fluid containing methacrylic acid. When isobutylene is fed in a gaseous state, the dissolution is carried out by a gas-liquid contact between isobutylene and methacrylic acid or isobutylene and process fluid. In this case, a method having a great contact area should be adopted. Thus, the dissolution can be practised more effectively if a packed tower or a special absorbing equipment such as spray type absorbing tower or static mixer is provided.

In order to achieve an appropriate velocity of reaction, the sulfonic acid group-containing ion exchange resin used in the invention should be a porous type having a great surface area. Particularly, sulfonic acid group-containing ion exchange resins having a specific surface area of 20 to 60 $m^2/g$, a pore diameter of 1,000 angstroms or below, a pore volume of 0.2 to 0.8 ml/g and an ion exchange capacity of 3 to 6 meg/g in the dry form are preferable because such resins have a practicable activity. For example, Amberlist-15 and IR-200cH manufactured by Rohm & Haas Co., Lewatit SPC-108 and 118 manufactured by Bayer Co., and Diaion RCP-150H manufactured by Mitsubishi Kasei Kogyo K.K. and the like can be used. In the reaction of this invention, there is a tendency that a catalyst having a higher activity has a lower selectivity based on isobutylene. Accordingly, a catalyst having an appropriate activity while satisfying an industrial productivity is more preferable.

Although the above-mentioned ion exchange resins can behave as the catalyst of the invention whether they are in the dry form or in the hydrated form, it is preferable to use the resins after dehydrating them by an appropriate procedure in order to obtain t-butyl methacrylate in a high yield from the start of the reaction. As the method of dehydration, the usually well known methods such as the heating under reduced pressure, azeotropic dehydration using a hydrocarbon solvent, washing with a polar solvent, and the like can be employed, though the method of dehydration is not limited to above and any methods may be used so far as water content in the resins can effectively be reduced by the methods. Said ion exchange resin simultaneously exhibits a catalytic activity on the t-butyl alcohol-forming addition reaction of isobutylene and water in the system and on its reverse reaction, as the result of which the activity on the reaction forming the objective t-butyl methacrylate is greatly deteriorated and, at the same time, the selectivity toward the t-butyl methacrylate based on isobutylene is also lowered. Accordingly, contamination of the reaction system by water and t-butyl alcohol must be avoided as possible. In order to achieve a particularly high economicity and industrial productivity by the continuous reaction of the invention, the total molar number of water and t-butyl alcohol in the process fluid should preferably 0.02 mole or less based on 1 mole of the total molar number of methacrylic acid and t-butyl methacrylate.

In carrying out the continuous reaction according to the invention, any of the piston flow type reaction or the circulation type reaction using a fixed bed reactor and the mixing type reaction using fluidized bed reactor may be used, and their appropriate combination may also be used. In order to control the selectivity of reaction, the reaction temperature must be maintained properly. For this purpose, it is preferable to have a cooling section capable of effectively removing the heat of reaction in the reaction system.

Particularly in the case of continuous flow type reaction where the mass transfer velocity on ion exchange resin catalyst is low, the use of shell-and-tube heat exchanger type reactor or multistage reactor equipped with intermediate cooling zone is effective. Since the main reaction of the invention forming t-butyl methacrylate is an equilibrium reaction and its exotherm is correlated to conversion of the reaction, an appropriately combined use of circulation or mixing type reaction and piston flow type reaction in accordance with conversion is more preferable because it facilitates the control of exotherm and enables to obtain an appropriate velocity of reaction.

If the removal of heat of reaction is not effective and the reaction temperature ascends unnecessarily, the oligomerization of isobutylene is accelerated, due to which the selectivity toward t-butyl methacrylate becomes low and no high yield can be achieved.

As above, the continuous reaction can be practised under various conditions. In order to obtain the objective compound in a high selectivity, the reaction conditions must be controlled strictly. In preliminary experiments, the present inventors found that t-butyl methacrylate of high quality can be obtained in a high productivity and a high yield only when the velocity of reaction is sufficiently high and the selectivity toward triisobutylene formed by the reaction is not higher than 2.5%. The inventors studied the reaction conditions in detail in order to find out the conditions meeting with the abovementioned object such as temperature, molar ratio of reactants, contact time with catalyst and the relations between molar ratio, conversion and selectivity. As the result, it was found that the selectivity toward triisobutylene can be made 2.5% or less if the following specified relation:

$$y < 100 - 50x$$

is satisfied, wherein x is ratio of the total molar number of isobutylene and its reaction products to the total molar number of methacrylic acid and its reaction products and y is conversion (%) of isobutylene. A part of the results of this detailed experiment is shown in Table 1. This experiment was carried out as a circulation type reaction using a fixed bed reactor filled with Amberlist-15 manufactured by Rohm & Haas Co.

TABLE 1

| Run No. | Molar ratio (x) | Reaction temperature (°C.) | Contact time (hours) | Conversion of isobutylene (%) | Selectivity (%) based on isobutylene | | | |
|---|---|---|---|---|---|---|---|---|
| | | | | | t-Butyl methacrylate | t-Butyl alcohol | Diisobutylene | Triisobutylene |
| 1 | 0.22 | 22~25 | 1.0 | 82.3 | 83.9 | 0.6 | 12.2 | 3.3 |
| 2 | 0.30 | −1~1 | 3.0 | 78.2 | 89.6 | 0.8 | 9.6 | <0.05 |
| 3 | 0.42 | 1~3 | 2.5 | 75.8 | 86.2 | 1.2 | 10.7 | 1.9 |
| 4 | 0.41 | 1~3 | 3.2 | 83.1 | 84.0 | 1.1 | 12.1 | 2.8 |
| 5 | 0.46 | 10~12 | 0.7 | 66.7 | 83.9 | 0.7 | 13.9 | 1.5 |
| 6 | 0.54 | 10~13 | 2.1 | 74.8 | 80.9 | 0.9 | 14.3 | 3.9 |
| 7 | 0.51 | 0~3 | 1.4 | 53.2 | 89.8 | 1.1 | 9.1 | <0.05 |
| 8 | 0.73 | 6~8 | 2.0 | 60.3 | 81.9 | 1.2 | 15.1 | 1.8 |
| 9 | 0.76 | 6~8 | 2.7 | 65.2 | 79.9 | 0.9 | 16.0 | 3.2 |
| 10 | 0.81 | 7~8 | 1.5 | 49.7 | 83.7 | 1.0 | 14.6 | 0.7 |
| 11 | 0.92 | 1~5 | 1.1 | 24.1 | 84.9 | 1.0 | 14.1 | <0.05 |
| 12 | 1.04 | 10~12 | 0.7 | 35.0 | 82.0 | 0.9 | 16.3 | 0.8 |

It is apparent from Table 1 that, if the condition of $y < 100 - 50x$ is not satisfied, formation of triisobutylene markedly increases even if other reaction conditions are fixed. Since triisobutylene is quite difficult to separate as has been mentioned above, such large a formation of triisobutylene much lowers the yield of high quality t-butyl methacrylate.

On the other hand, the selectivity based on isobutylene ascends when x and y become smaller, but productivity decreases generally under such a condition. Accordingly, in order to achieve a high productivity from the industrial point of view, it is preferable to place certain limits upon x and y. In the range of $x < 0.25$, productivity is unsatisfactory even if conversion is high. In the range of $x > 1.0$, the process is operated at a low conversion, and the recovery of unreacted isobutylene requires an enlargement of equipments therefor which consumes an increased quantity of energies and results in a high cost. y is the main factor determining productivity in the range giving an adequate selectivity, and a higher value of ($x \times y$) gives a higher productivity.

From the practical viewpoint, the more preferable condition is $X \times y \geqq 20$.

As for reaction temperature, a temperature higher than 20° C. accelerates the oligomerization of isobutylene, so that formation of triisobutylene is high even if the above-mentioned condition is satisfied. If the temperature is lower than −20° C., on the other hand, no practicable reaction velocity can be achieved. Accordingly, the reaction temperature must be in the range of −20° C. to +20° C.

It should be noted here that, since the reaction of the invention is exothermic, the temperature at the outlet part of reactor, particularly fixed bed type reactor, is higher than the temperature at the inlet. In this invention, the temperatures at both inlet and outlet must be in the above-mentioned range. The temperature range particularly preferable from the practical viewpoint is −5° to +15° C. at the inlet area and −3° to +20° C. at the outlet area. Preferably, the temperature difference between inlet and outlet does not exceed 10° C.

In the process of the invention, the formed t-butyl methacrylate is obtained from the reaction mixture by previously degassing the unreacted isobutylene, stripping off the low boiling substances such as t-butyl alcohol, diisobutylene and optionally a mixture composed mainly of low boiling solvent, and thereafter distilling off the objective product in the t-butyl methacrylate purifying tower, while withdrawing the unreacted methacrylic acid from the bottom of the tower and circulating it into the reaction process. Since the formation of triisobutylene is kept low by strictly controlling the reaction conditions as above, no particular separation of triisobutylene is necessary in this case.

In the first place, one non-limitative example of the method for degassing and recovering the unreacted isobutylene from reaction mixture will be mentioned.

The liquid reaction mixture taken out of the reaction step is heated under a pressure equal to that of reaction system to degas the supersaturated unreacted isobutylene. In order to improve the yield, this is circulated into the reaction step. The temperature of the heating is preferably 110° C. or below, in order to prevent the polymerization of liquid reaction mixture. The degassed isobutylene is accompanied by the low boiling substances in the liquid reaction mixture, i.e. t-butyl alcohol and diisobutylene. If they are circulated into the reaction step as they are, these low boiling substances are concentrated in the reaction mixture, and the t-butyl alcohol disturbs the formation of t-butyl methacrylate and the diisobutylene causes the formation of triisobutylene. Accordingly, it is preferable to provide a cooler at the top of degassing plant to return the major part of t-butyl alcohol and diisobutylene into the degassing plant.

The liquid reaction mixture which has partially released the unreacted isobutylene still contains a considerable amount of unreacted isobutylene. Therefore, it is further degassed at a reduced pressure. This degassing under reduced pressure may be carried out simultaneously with the subsequent distillation under reduced pressure. Taking an improvement in yield into account, the isobutylene degassed under reduced pressure should also be recovered and circulated into the reaction step, preferably. This can be performed by passing it through a cooler placed in the exhaust gas side of vacuum apparatus.

The liquid reaction mixture from which isobutylene has been separated substantially completely is subjected to a distillation under reduced pressure to remove t-butyl alcohol, diisobutylene and sometimes a low boiling point mixture composed mainly of solvent, after which it is sent to purifying tower where unreacted methacrylic acid is withdrawn from tower bottom and t-butyl methacrylate is obtained as the product.

The separated unreacted methacric acid is contaminated by a small amount of t-butyl methacrylate and triisobutylene. After subtracting a part of it, the remainder may be directly circulated into the reaction step. Otherwise, it is also possible to subject it to a simple distillation to remove the high boiling residue therefrom and thereafter circulate the remainer into the reaction step. When the process of the invention has reached a steady state, a part or the whole of the triisobutylene formed in the reaction comes to contaminate the product. However, in the process of the invention, the formation of triisobutylene is very slight, so that it does not affect the quality of product greatly even if its whole quantity enters the product. In practising the process of the invention, polymerization must be prevented particularly in the steps of degassing and distillation. For this purpose, dissolution of an appropriate quantity of oxygen or addition of a necessary quantity of appropriate polymerization inhibitor such as hydroquinone, hydroquinone monomethyl ether and the like is effective. Optionally, they may be added to the starting methacrylic acid.

Figure 2:
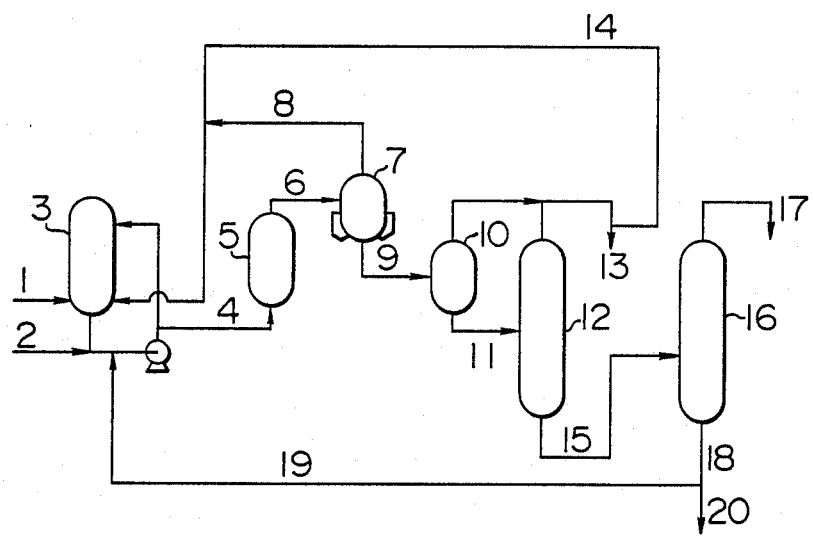
FIG. 2 is a diagram illustrating one example of the production process of t-butyl methacrylate according to the present invention, wherein the numerical figures have the following meanings.

FIG. 2 illustrates one example of the production process of t-butyl methacrylate according to the invention. It will be explained below.

Isobutylene is fed from line 1 and methacrylic acid is fed from line 2, both continuously. A liquid solution of isobutylene and methacrylic acid is prepared in the circulation-absorption system involving absorbing tower 3, which is taken out from line 4 and passed through reactor 5 filled with catalyst to make progress the reaction. The liquid reaction mixture is fed through line 6 into degassing plant 7, and the degassed unreacted isobutylene is circulated via line 8 into the reaction step. The partially degassed liquid reaction mixture is fed via line 9 into vacuum degassing plant 10 where the residual unreacted isobutylene is degassed almost completely. Subsequently, it passes line 11 and reaches low boiling fraction stripping tower 12 where it is distilled under reduced pressure. Thus, a fraction composed mainly of t-butyl alcohol and diisobutylene is distilled out from line 13. The unreacted isobutylene which has been degassed in the vacuum degassing plant 10 is circulated via line 14 into the reaction step. The liquid reaction mixture which has released low boiling substances is fed via line 15 into t-butyl methacrylate purifying tower 16, where it is distilled under reduced pressure. The product, i.e. t-butyl methacrylate, is taken out via line 17. The unreacted methacrylic acid is taken out from line 18, and its major part is circulated into reaction step via line 19, while its minor part is taken out of the system via line 20.

As above, the process of the invention performs the reaction in a high selectivity. Because the unreacted material is effectively recovered and circulated, the process of the invention gives a high yield. Further, it can yield t-butyl methacrylate in a high purity, has a high economicity, and is excellent in the industrial value.

Next, the process of the invention will be illustrated with reference to the following non-limitative examples.

EXAMPLE 1

A 60 mm φ cylindrical reactor was filled with 150 g of a sulfonic acid group-containing ion exchange resin (IR-200cH, manufactured by Rohm & Haas Co.) which had been dehydrated to a water content of 1% or below and dried. Into the tower bottom part of an absorbing tower (25 mm φ×500 mm) filled with Rasching rings, the starting isobutylene was fed at a flow rate of 27.1 liters/hour in the normal state and, at the same time, the isobutylene recovered in the degassing step was circulated. Into the tower top part, the starting methacrylic acid was fed at a rate of 103.5 g/hour and, at the same time, the methacrylic acid recovered in the distillation step was circulated, and further the tower bottom liquid was circulated at a rate of 25 liters/hour. Temperature of the tower bottom liquid was controlled so as to become 0° C.

The tower bottom liquid of the absorbing tower was continuously withdrawn at a rate of 520 g/hour and fed into reactor upflow-wise. The liquid reaction mixture was externally circulated so that its flow rate in reactor came to 10 liters/hour and the inlet temperature of reactor was controlled so as to become 0° C. by means of heat exchanger. At this time, the temperature in the reactor was 0° C. at the inlet part and 3° C. at the outlet part. The liquid reaction mixture stationarily withdrawn from the reactor at a rate of 520 g/hour had the composition shown in Table 2. From the composition, the molar ratio of reactants x was calculated as 0.43, and conversion of isobutylene y was calculated as 66.0%. These values satisfied the condition y<100−50x.

TABLE 2

| Component | Content (% by weight) |
| --- | --- |
| Isobutylene | 7.7 |
| t-Butyl alcohol | 0.2 |
| Diisobutylene | 1.0 |
| Triisobutylene | 0.6 |
| t-Butyl methacrylate | 32.2 |
| Methacrylic acid | 58.3 |

The liquid reaction mixture was continuously fed into the jacketed degassing plant equipped with a stirrer and heated so as to keep an inner temperature of 90° C. The isobutylene which had been degassed, passed through cooler and was circulated into the absorbing tower had a flow rate of 5.9 liters/hour in the normal state. The liquid reaction mixture taken out from the degassing plant by the method of overflow was subsequently treated adiabatically under a reduced pressure of 80 mm Hg, where isobutylene was degassed at a flow rate of 8.8 liters/hour in the normal state. The degassed isobutylene was circulated from the exhaust gas side of vacuum pump via cooler to the absorbing tower of reaction step. By the two-stage degassing procedure, isobutylene concentration in the liquid reaction mixture was reduced to 0.65%. Subsequently, the liquid reaction mixture was fed into the 10th tray of oldershow type distillation tower having 15 trays and distilled at a reflux ratio of 8 under a reduced pressure of 80 mm Hg to separate a liquid having a boiling point of 60° C. and a composition shown in Table 3 as a distillate at a rate of 9.5 g/hour.

TABLE 3

| Component | Content (% by weight) |
| --- | --- |
| t-Butyl alcohol | 8.4 |
| Diisobutylene | 54.8 |
| t-Butyl methacrylate | 35.2 |
| Others | 1.6 |

Subsequently, the bottom liquid was fed into the 3rd tray of Oldershow type distillation tower having 15 trays and distilled at a reflux ratio of 3 under a reduced pressure of 30 mm Hg to obtain purified t-butyl methacrylate at a boiling point of 49° C. at a rate of 146 g/hour. Quality of the t-butyl methacrylate thus obtained is shown in Table 4.

TABLE 4

| Component | Content (% by weight) |
| --- | --- |
| t-Butyl methacrylate | 99.66 |
| Diisobutylene | 0.02 |
| Triisobutylene | 0.29 |
| Methacrylic acid | 0.03 |

The bottom liquid of the product purifying tower was obtained at a rate of 322 g/hour, of which 10 g/hour was withdrawn and the remainder was wholly circulated into the absoring tower of the reaction step. Composition of this bottom liquid is shown in Table 5.

TABLE 5

| Component | Content (% by weight) |
| --- | --- |
| t-Butyl methacrylate | 5.0 |
| Triisobutylene | 0.8 |
| Methacrylic acid | 92.6 |
| Others | 1.6 |

The yield of t-butyl methacrylate obtained by the above-mentioned process was 84.9% based on isobutylene and 85.4% based on methacrylic acid.

EXAMPLE 2

The first reactor (60 mm φ cylindrical reactor) was filled with 125 g of a sulfonic acid group-containing ion exchange resin (Amberlist-15, manufactured by Rohm & Haas Co.). The second reactor (jacketed 12 mm φ cylindrical reactor) was filled with 35 g of SPC-118 (manufactured by Bayer Co.) which had been dehydrated to a water content of 1% or below and dried. Into the tower bottom part of an absorbing tower (25 mm φ×500 mm) filled with Raschig rings, the starting isobutylene was fed at a rate of 32.7 liters/hour in the normal state and, at the same time, the isobutylene recovered in the degassing step was circulated. Into its tower top part, starting methacrylic acid was fed at a rate of 117 g/hour and, at the same time, the methacrylic acid recovered in the distillation step was circulated. The bottom liquid of the absorbing tower was withdrawn at a rate of 50 liters/hour and adjusted to a temperature of 5° C. by means of heat exchanger, after which it was fed to the top of the first reactor downflow-wise. After passing the first reactor, it was fed to the top of absorbing tower at a rate of 10 liters/hour and the remainder was circulated into the tower bottom. At this time, temperature of outlet part of the first reactor was 5° C., and temperature of bottom part of absorbing tower was 7° C. Subsequently, the liquid reaction mixture was continuously withdrawn from the outlet of the first reactor at a rate of 640 g/hour and fed into the second reactor upflow-wise to carry out a piston flow type reaction. At this time, the second reactor was controlled by flowing a coolant through the jacket so that the temperature of the liquid passing the outlet came to 8° C. The liquid reaction mixture stationarily withdrawn from the second reactor at a rate of 640 g/hour had the composition shown in Table 6.

TABLE 6

| Component | Content (% by weight) |
|---|---|
| Isobutylene | 18.2 |
| t-Butyl alcohol | 0.3 |
| Diisobutylene | 0.9 |
| Triisobutylene | 0.5 |
| t-Butyl methacrylate | 32.1 |
| Methacrylic acid | 48.0 |

From the composition, molar ratio of reactants was calculated as 0.72, and conversion of isobutylene was calculated as 44.0%.

Subsequently, the liquid reaction mixture was continuously fed into a jacketed degassing plant having a stirrer and heated so as to maintain an inner temperature of 90° C. The isobutylene which has been degassed, passed the cooler and was circulated into absorbing tower had a flow rate of 35.4 liters/hour in the standard state. The liquid reaction mixture taken out from the degassing plant by the method of overflow was subsequently treated adiabatically under a reduced pressure of 80 mm Hg in the same vacuum system as for the low boiling fraction stripping tower, whereby isobutylene was degassed at a flow rate of 9.7 liters/hour in the normal state. The degassed isobutylene was circulated from the exhaust gas side of vacuum pump via a cooler into the absorbing tower of reaction step together with the vacuum system of the low boiling fraction stripping tower. As the result, the isobutylene concentration in the liquid reaction mixture reached 0.7% by weight.

Subsequently, the liquid reaction mixture was fed into the 10th tray of a 15 tray Oldershow type distillation tower and distilled under a reduced pressure of 80 mm Hg at a reflux ratio of 5. As the result, a liquid having a boiling point of 63° C. and the composition shown in Table 7 was separated as distillate at a rate of 18 g/hour.

TABLE 7

| Component | Content (% by weight) |
|---|---|
| t-Butyl alcohol | 5.9 |
| Diisobutylene | 28.1 |
| t-Butyl methacrylate | 63.8 |
| Others | 2.2 |

Subsequently, the bottom liquid was fed to the 3rd tray of a 15 tray Oldershow type distillation tower and distilled under a reduced pressure of 30 mm Hg at a reflux ratio of 2 to obtain purified t-butyl methacrylate at a boiling point of 49° C. at a rate of 176 g/hour. Quality of the t-butyl methacrylate thus obtained is shown in Table 8.

TABLE 8

| Component | Content (% by weight) |
|---|---|
| t-Butyl methacrylate | 99.58 |
| Diisobutylene | 0.03 |
| Triisobutylene | 0.34 |
| Methacrylic acid | 0.05 |

Subsequently, the bottom liquid of the product purifying tower was fed into a flash still and subjected to a flash vaporization under a reduced pressure of 30 mm Hg. The distillate having the composition shown in Table 9 was obtained at a rate of 324 g/hour and its whole quantity was circulated into the absorbing tower of reaction step.

TABLE 9

| Component | Content (% by weight) |
|---|---|
| t-Butyl methacrylate | 5.3 |
| Triisobutylene | 0.8 |
| Methacrylic acid | 93.9 |

Yield of the t-butyl methacrylate obtained by this process was 84.8% based on isobutylene and 91.2% based on methacrylic acid.

COMPARATIVE EXAMPLE 1

The reaction of Example 2 was repeated, except that, in the reaction step, the starting isobutylene was fed at a rate of 29.3 liters/hour in the normal state and the starting methacrylic acid was fed at a rate of 90.9 g/hour. The temperature of liquid passing through the first reactor was 5° C., and bottom temperature of absorbing tower was 6° C. The liquid reaction mixture which was withdrawn from the first reactor and had passed the second reactor had a flow rate of 239 g/hour. Composition of this liquid reaction mixture is shown in Table 10.

TABLE 10

| Component | Content (% by weight) |
|---|---|
| Isobutylene | 2.5 |
| t-Butyl alcohol | 0.3 |
| Diisobutylene | 4.6 |
| Triisobutylene | 5.4 |
| t-Butyl methacrylate | 57.1 |
| Methacrylic acid | 30.1 |

From the composition, molar ratio of the reactants x was calculated as 0.68, and conversion of isobutylene y was calculated as 95.3%. These values did not satisfy the condition of the invention, i.e. $y < 100 - 50x$.

This liquid reaction mixture was after-treated in the same manner as in Example 2. The unreacted isobutylene was recovered by a treatment under a reduced pressure of 80 mm Hg, and its flow rate was 1.1 liters/hour in the normal state. In the low boiling fraction stripping tower, the fraction shown in Table 11 was obtained at a rate of 31 g/hour.

TABLE 11

| Component | Content (% by weight) |
|---|---|
| t-Butyl alcohol | 1.6 |
| Diisobutylene | 34.4 |
| t-Butyl methacrylate | 62.5 |
| Others | 1.5 |

In the t-butyl methacrylate purifying tower, a fraction having the composition shown in Table 12 was obtained as the product at a rate of 122 g/hour.

TABLE 12

| Component | Content (% by weight) |
|---|---|
| t-Butyl methacrylate | 93.44 |
| Diisobutylene | 0.04 |
| Triisobutylene | 5.94 |
| Methacrylic acid | 0.58 |

By flash vaporization of the bottom liquid obtained from the product purifying tower, a distillate having the composition shown in Table 13 was obtained at a rate of 70 g/hour. It was circulated into the absorbing tower of the reaction step.

TABLE 13

| Component | Content (% by weight) |
|---|---|
| t-Butyl methacrylate | 3.4 |
| Triisobutylene | 7.7 |
| Methacrylic acid | 88.9 |

Yield of the t-butyl methacrylate obtained by this process was 61.3% based on isobutylene and 75.9% based on methacrylic acid.

COMPARATIVE EXAMPLE 2

In this example, an example of production of t-butyl methacrylate by batch-wise reaction and distillation will be mentioned.

Into a 2 liter four-necked flask equipped with a stirrer was charged 688 g (8 moles) of metharylic acid, 80 g of n-hexane, 1 g of hydroquinone monomethyl ether and 120 g of a sulfonic acid group-containing ion exchange resin (IR-200cH, manufactured by Rohm & Haas Co.). While stirring the mixture and maintaining an inner temperature of 5° C., isobutylene was blown thereinto for 3.5 hours at a rate of 20 liters/hour in the normal state. After stopping to feed isobutylene, the stirring was continued for 16.5 hours at an inner temperature of 5° C. to make progress the reaction. After the reaction, the liquid reaction mixture was separated by decantation, and the residual catalyst and reused as it was to repeat the batch reaction 12 times in the total, throughout which the other reaction procedures were just the same as in the first reaction. After the 12th reaction had been completed, 1,084 g of liquid reaction mixture was obtained. Its composition was as shown in Table 14.

TABLE 14

| Component | Content (% by weight) |
|---|---|
| n-Hexane | 7.3 |
| Isobutylene | 1.5 |
| Diisobutylene | 3.5 |
| t-Butyl alcohol | 1.1 |
| Triisobutylene | 2.4 |
| t-Butyl methacrylate | 54.1 |
| Methacrylic acid | 30.1 |

It is apparent from Table 14 that molar ratio of isobutylene components to methacrylic acid components (x) was 0.72 and conversion of isobutylene (y) was 94.9%. Then, 867 g of this liquid reaction mixture was introduced into one liter four-necked flask and fractionally distilled under a reduced pressure by the use of a 24 mm $\phi$ 15 tray Oldershow type distillation tower.

First, unreacted isobutylene and n-hexane were distilled off, and then the system was gradually evacuated to distil out the low boiling substances till the tower top temperature reached 53° C. at a pressure of 50 mm Hg at a reflux ratio of 10. Subsequently, the pressure was lowered to 30 mm Hg, and at this pressure distillation was carried out at a reflux ratio of 2 to obtain 406 g of a product fraction having the composition shown in Table 15 at a tower top temperature of 49° C. Then, still at a pressure of 30 mm Hg, distillation was carried out at a reflux ratio of 10 till the tower top temperature reached 73° C., in order to separate the impurity triisobutylene. Table 16 illustrates the composition of the 43 g of distillate obtained by this procedure. Finally, distillation was carried out at a reduced pressure of 20 mm Hg at a reflux ratio of 0.5 to recover 247 g of a recovered methacrylic acid fraction having the composition shown in Table 17. The residue of this distillation weighed 23 g. The last distillate was regarded as reusable as starting compound of the reaction. Yield of t-butyl methacrylate obtained of this process was 62.4% based on isobutylene and 80.5% based on methacrylic acid.

TABLE 15

| Component | Content (% by weight) |
|---|---|
| t-Butyl methacrylate | 98.69 |
| t-Butyl alcohol | 0.13 |
| Diisobutylene | 0.44 |
| Triisobutylene | 0.41 |
| Methacrylic acid | 0.33 |

TABLE 16

| Component | Content (% by weight) |
|---|---|
| t-Butyl methacrylate | 55.9 |
| Triisobutylene | 39.5 |
| Methacrylic acid | 4.6 |

TABLE 17

| Component | Content (% by weight) |
|---|---|
| t-Butyl methacrylate | 1.8 |
| Triisobutylene | 2.1 |
| Methacrylic acid | 96.1 |

What is claimed is:

1. A process for producing t-butyl methacrylate by a continuous process which comprises reacting methacrylic acid and isobutylene in the presence of a sulfonic acid group-containing ion exchange resin while controlling the reaction at a reaction temperature of $-20°$ C. to $+20°$ C. so as to satisfy the following condition:

$$y < 100 - 50x$$

wherein x is the ratio of the total molar number of isobutylene and its reaction products to the total molar number of methacrylic acid and its reaction products and y is conversion (%) of isobutylene, followed by degassing the unreacted isobutylene, removing the low boiling substances by distillation under reduced pressure, and then sending the remainder to a t-butyl methacrylate purifying tower where a product of high purity is withdrawn from the distillate side and unreacted methacrylic acid is withdrawn from the tower bottom side and circulated to the reaction step.

2. A process according to claim 1, wherein said reaction of methacrylic acid and isobutylene is carried out in a fixed bed reactor filled with sulfonic acid group-containing ion exchange resin.

3. A process according to claim 2, wherein said reaction of methacrylic acid and isobutylene is carried out by elevating the temperature so that the reaction temperature of a fixed bed reactor comes to $-5°$ to $+15°$ C. at the inlet of the reactor and $-3°$ to $+20°$ C. at the outlet and the temperature difference between inlet and outlet comes to 10° C. or below.

4. A process according to claim 1, wherein, regarding the x and y satisfying $y < 100 - 50x$, x is in the range of 0.25 to 1.0 and $(X \times y)$ satisfies $(X \times y) > 20$.

5. A process according to claim 1, wherein the selectivity toward the triisobutylene formed by the reaction is 2.5% or below based on isobutylene.

* * * * *